United States Patent
Schwabe

(12) 
(10) Patent No.: US 6,328,999 B1
(45) Date of Patent: Dec. 11, 2001

(54) GINKGO BILOBA LEAF EXTRACTS WITH A REDUCED 4'-O-METHYLPYRIDOXINE AND BIFLAVONE CONTENT

(75) Inventor: Klaus-Peter Schwabe, Karlsruhe (DE)

(73) Assignee: Dr. Willmar Schwabe GmH & Co., Karlsruhe (DE)

( * ) Notice: Subject to any disclaimer, the term of this patent is extended or adjusted under 35 U.S.C. 154(b) by 0 days.

(21) Appl. No.: 09/555,235

(22) PCT Filed: Dec. 18, 1998

(86) PCT No.: PCT/DE98/03790

§ 371 Date: May 25, 2000

§ 102(e) Date: May 25, 2000

(87) PCT Pub. No.: WO99/32129

PCT Pub. Date: Jul. 1, 1999

(30) Foreign Application Priority Data

Dec. 19, 1997 (DE) .............................................. 197 56 848

(51) Int. Cl.⁷ .......................... A61K 35/78; A01N 65/00
(52) U.S. Cl. ................................. 424/752; 514/27
(58) Field of Search ................................. 424/752; 514/27

(56) References Cited

U.S. PATENT DOCUMENTS

| 4,981,688 | | 1/1991 | Ayroles et al. . | |
| 5,399,348 | * | 3/1995 | Schwabe | 514/27 |
| 5,885,582 | * | 3/1999 | O'Reilly | 514/25 |
| 6,001,393 | * | 12/1999 | Daoud | 424/489 |
| 6,030,621 | * | 2/2000 | Long et al. | 514/27 |
| 6,117,431 | * | 9/2000 | Ramazanov et al. | 424/195.1 |
| 6,174,531 | * | 1/2001 | Zhang et al. | 514/27 |

FOREIGN PATENT DOCUMENTS

| 2031384 | 6/1991 | (CA) . |
| 2031385 | 6/1991 | (CA) . |
| 2031386 | 6/1991 | (CA) . |
| 0 402 925 A2 | 12/1990 | (EP) . |

OTHER PUBLICATIONS

Chemical Patent Index, DocumentationAbstracts Journal, Derwent Publication. London, 1996, No. 96–038147/04.

Ansgar Arenz et al., Occurrence of Neurotoxic 4'–O–Methylpyhridoxine in Ginkgo biloba Leaves, Ginkgo Medications and Japanese Ginkgo Food, Planta Medica 62 (1996) 548–551.

* cited by examiner

Primary Examiner—Herbert J. Lilling
(74) Attorney, Agent, or Firm—Workman, Nydegger & Seeley

(57) ABSTRACT

The invention relates to extracts from ginkgo biloba leaves with a reduced 4'-O-methyl pyridoxine and biflavones content, to a method for the production thereof and to medicaments containing said extracts.

10 Claims, No Drawings

GINKGO BILOBA LEAF EXTRACTS WITH A REDUCED 4'-O-METHYLPYRIDOXINE AND BIFLAVONE CONTENT

BACKGROUND OF THE INVENTION

1. Field of the Invention

The present invention relates to extracts of ginkgo biloba leaves with reduced 4'-O-methyl pyridoxine and biflavones content, a process for their preparation and medicaments comprising said extracts, which do not exhibit undesirable side effects initiated by 4'-O-methyl pyridoxine and biflavones even at high dosages.

2. Present State of the Art

Extracts of Ginkgo biloba leaves have been used therapeutically for 30 years. The Commitee E of the Federal Health Office (Bundesgesundheitsamt) in Berlin has acknowledged that medicaments comprising defined extracts are effective in the symptomatic treatment of performance disturbances caused by cerebral insufficiency, peripheral occlusive disease, vertigo and tinnitus (BAnz No. 133, Jul. 19, 1994). These extracts are characterized by a content of 22 to 27% flavone glycosides, 5 to 7% terpene lactones, 2.8 to 3.4% thereof being ginkgolides A, B and C, and 2.6 to 3.2% bilobalide, and by a maximum content of 5 ppm ginkgolic acids (alkyl phenol compounds). Such extracts of Ginkgo biloba leaves and methods for their preparation are known from DE 39 40 091 (EP-B-0 431 535) and DE 39 40 092 (EP-30 B-0 431 536).

The occurence of 4'-methoxy pyridoxine (4'-O-methyl pyridoxine) in ginkgo biloba seeds has been described by Wada et al., Chem. Pharm. Bull. 33 (1985), 3555–3557. This compound causes symptoms of poisoning like convulsions and unconsciousness ("Gin-nan food poisoning" and "Gin-nan sitotoxism"), which may occur after consumption of larger amounts of ginkgo seeds. Therefore, the discoverer of this compound named it "ginkgotoxin". In a later work the same research group found out that 4'-O-methyl pyridoxine is absent in ginkgo leaves (Wada et al., Biol. Pharm. Bull. 16 (1993), 210–212). Contrary to this statement is a recently issued publication reporting on the isolation and identification of 4'-O-methyl pyridoxine from ginkgo leaves (Arenz et al., Planta Medica 62 (1996), 548–551). In this work commercial preparations with extracts of ginkgo biloba leaves have been analyzed with respect to their anti-vitamin $B_6$ (4'-O-methyl pyridoxine) content and concentrations of between about 4 and 10 $\mu$g/ml of liquid medicinal form have been found. This corresponds to a concentration of about 100 to 250 ppm in the dry extracts processed to preparations.

DETAILED DESCRIPTION OF THE PREFERRED EMBODIMENTS

Ginkgo extracts used for therapy comprise additionally up to 1000 ppm biflavones. Our own investigations have surprisingly revealed that in addition to biological activities known from literature these compounds also show immunotoxicologic effects. In an popliteal lymph node assay in mice we have observed that the ethyl acetate soluble fraction of an ethanol-water total extract of ginkgo leaves causes a lymph node reaction; see example 1. Testing of the subfractions obtained by chromatographic separation revealed that the inunnotoxicologic effect merely occurred after application of the subfraction which contained more than 70% biflavones. The biflavones found in ginkgo are the following compounds: sciadopitysin, ginkgetin, isoginkgetin, sequoiaflavone and bilobetin.

The technical problem underlying the present invention is to provide an extract of ginkgo biloba leaves being virtually free of 4'-O-methyl pyridoxine and alkyl phenol compounds (ginkgolic acids, ginkgol), having the technically feasible minimum biflavone content and the flavonol glycosides and terpene lactones, which are the acknowledged activity-determining ingredients, in concentrations demanded by the Commitee E (BAnz No. 133, Jul. 19, 1994). The extract according to the present invention contains:

20 to 30% by weight flavonol glycosides a total of 2.5 to 4.5% by weight of ginkgolides A, B, C and J 2.0 to 4.0% by weight bilobalide below 10 ppm, preferably below 1 ppm alkyl phenol compounds (ginkgolic acids, ginkgol)

below 10% by weight proanthocyanidins below 50 ppm 4'-O-methyl pyridoxine below 100 ppm biflavones The present invention further relates to a method for the preparation of such an extract of ginkgo biloba leaves.

This technical problem is solved in that in the known method for the preparation of ginkgo extracts two additional process steps are introduced:

1. treatment with cation exchanger to remove 4'-O-methyl pyridoxine
2. adsorption of the biflavones on activated charcoal These measures are practiced in the process according to claim 3 of DE 39 40 091 preferably before or after step g). Accordingly, after the filtration of the solution obtained in step f) said solution is passed through a cation exchange column and the column is eluted with aqueous ethanol or aqueous methanol. The obtained eluate is treated with activated charcoal. For the elution of the cation exchanger an aqueous solution containing 20 to 80% by weight, preferably 50% by weight ethanol or methanol can be used. The sequence of the two steps according to the present invention is interchangeable without altering the result. Thereafter work is continued according to example 3, below, and the solution is extracted with an aliphatic or cycloaliphatic solvent to remove the alkyl phenol compounds.

Step c) of the method serves to remove lipophilic components, which are poorly soluble in water, including the major amount of biflavones.

The preferred method for the preparation of an extract of the present invention is therefore characterized by the number and order of the following steps:

a) extraction of ginkgo biloba leaves with aqueous acetone, an aqueous alkanol having 1 to 3 carbon atoms or absolute methanol, b) separating the organic solvent by concentrating the solvent up to a content of not more than 10% by weight, wherein water can be added in the last distillation steps, c) diluting the remaining aqueous solution with water to a content of solids of 5 to 25% by weight, cooling to a temperature of below 25° C. and allowing it to stand until a precipitate forms, d) a treatment of the remaining aqueous solution with ammonium sulfate and thereafter at least one extraction with methyl ethyl ketone or a mixture of methyl ethyl ketone and acetone, e) concentrating the obtained extract and diluting with an ethanol-water mixture to a solution containing each 50% by weight water and ethanol and 10% by weight of solids, f) treatment of the solution with a lead compound or an insoluble polyamide, g) filtration of the solution and passage through a strongly acidic cation exchanger, elution of the cation exchanger with aqueous ethanol or aqueous methanol, h) treating the eluate with activated charcoal, i) extraction of the filtered solution with an aliphatic or cycloaliphatic solvent having a boiling point of 60 to 100° C., j) concentrating the remaining aqueous-alcoholic solution, subsequently treating with ammonium sulfate and extraction with methyl ethyl ketone and ethanol, k) concentrating the obtained organic phase to a content of solids of 50 to 70% by weight, and l) drying the concentrate under vacuum to a dry extract having a water content of below 5 %.

In a further embodiment of the present invention, steps g) and h) are interchanged. In a further embodiment of the present invention, steps g) and h) of the method are performed 20 only after step i).

In the known methods for enrichment of flavonol glycosides and terpene lactones by adsorption resins (EP-B-0 360 556, JP-A-04182434) the two steps according to the present invention are performed with the methanolic-aqueous solution of the extracts from the desorption step (cf EP-B-0 360 556, example III, claim 12) and the ethanolic-aqueous solution according to JP-A-04182434, respectively. Examples of useful cation exchangers are acidic cation exchangers. The most preferred cation exchanger is a strongly acidic cation exchanger like Merck I.

The extract prepared according to the present invention demonstrates in pharmacological test models circulation promoting-, ischemia damages preventing-, radical scavenger-, and thrombocyte aggregation inhibiting-properties, where in contrast to hitherto known ginkgo extracts even at high dosage no undesirable effects can occur, which may be induced by 4'-O-methyl pyridoxine and biflavones.

Furthermore, the present invention relates to medicaments characterized by the presence of ginkgo biloba extract according to the present invention.

For the preparation of medicaments the extract according to the present invention may be conventionally processed, e.g. into solutions, coated tablets, tablets or preparations for injection. The medicaments may be used for the treatment of peripheral and cerebral arterial circulatory disorders.

EXAMPLE 1

Popliteal lymph node test: male C57BL/6 mice of 18 to 24 g have been used (Charles River, Sulzfeld). The animals were kept under standardized environmental conditions having free access to food and water. For induction of the popliteal lymph node reaction (PLR) the test substances in 10 µl DMSO have been injected subplantar into the left hind paw. The animals of the control group merely obtained one injection of 10 µl DMSO. Of the single extracts each has been administered in 2 mg portions. The dose for the different subextracts corresponded to their respective proportion in the starting extract. After seven days the test animals have been killed by cervical dislocation under ether anesthesia. Both popliteal lymph nodes have been removed and collected on moistened filter paper in petri dishes after removal of adhering tissue. The weight of the lymph nodes has been determined immediately afterwards on an electronic balance having a sensibility of 0.1 mg. The PLR strength is indicated as the weight difference of the ipsilateral and contralateral popliteal lymph nodes.

| Substance | Dose | weight of lymph node (mg) |
| --- | --- | --- |
| ethyl acetate fraction | 2.00 mg | 4.2 mg |
| biflavone fraction | 0.35 mg | 3.4 mg |

EXAMPLE 2

2.5 g activated charcoal are added to 250 ml supernatant of the lead-tannin-precipitation according to example 1 of DE 39 40 091 (col. 4, 1. 67), containing 10% dry residue in the solution with 50% by weight ethanol. This mixture is stirred at room temperature for 30 minutes. The activated charcoal is filtered off and the filtrate is passed through a column loaded with 20 ml of strongly acidic cation exchanger (Merck I). The eluted solution is further treated according to the process described in example 1 of DE 39 40 091.

22.25 g dry extract having a content of 23.9% ginkgo flavonglycosides, 3.3% ginkgolides, 2.9% bilobalide, 7.1% proanthocyanidins, below 1 ppm alkyl phenol compounds, below 50 ppm*) 4'-O-methylpyridoxine and 60 ppm biflavones **) are obtained after drying the solution of the final product in methyl ethyl ketone/ethanol.

EXAMPLE 3

250 ml 90% methanolic-aqueous solution from the desorption of the flavones and terpene lactones from the adsorber resin Duolite S-761 according to example III, page 5, line 41 of EP-B-0 360 556, containing 10% dry residue in 90% by weight methanol, are filtered through a column loaded with 15 ml strongly acidic cation exchanger. By adding 3.75 g activated charcoal a part of the methanol is removed from this solution under vacuum, by adding water the solution is adjusted to a methanol concentration of 50% by weight and stirred for 30 minutes at room temperature. The activated charcoal is filtered off by means of suction through a filter bed and rinsed with 20 ml 50% methanol. 23.2 g ginkgo extract having a content of 22.8% ginkgo flavoneglycosides, 3.1% ginkgolides, 2.8% bilobalide, 9.6 % proanthocyanidins, below 1 ppm alkyl phenol compounds, below 50 ppm 4'-O-methylpyridoxine and 28 ppm biflavones are obtained after concentrating the solutions to dryness under vacuum.

EXAMPLE 4

Formulation for ginkgo extract tablets:

| ingredient | mg/core |
| --- | --- |
| ginkgo extract | 80.0 |
| lactose DAB 10***) | 40.0 |
| silica DAB 10 | 20.0 |
| microcrystalline cellulose DAB 10 | 84.0 |
| corn starch DAB 10 | 25.0 |
| croscarmellose NF | 10.0 |
| purified water DAB 10 | (40.0) |
| magnesium stearate DAB 10 | 1.0 |
| | 260.0 |

*)method of analysis according to Arenz et al., Planta Medica, Vol. 62 (1996), 548–551
**)method of analysis according to Gobbata et al., Fitoterapia, Vol. 67 (1996), 152–158
***)DAB 10 = Deutsches Arzneibuch 10 = German Pharmacopoeia 10

The ingredients are mixed, granulated with water according to common procedures in a mixer or vortex spray device and afterwards tabletted on a rotary pelleting press.

What is claimed is:

1. Extract from ginkgo biloba leaves comprising:
   20 to 30% by weight flavonol glycosides
   a total of 2.5 to 4.5% by weight of ginkgolides A, B, C and J
   2.0 to 4.0% by weight bilobalide
   below 10 ppm alkyl phenol compounds
   below 10% by weight proanthocyanidins
   below 50 ppm 4'-O-methyl pyridoxine
   below 100 ppm biflavones.

2. Method for the preparation of an extract comprising:
a) extraction of ginkgo biloba leaves with aqueous acetone, an aqueous alkanol having 1 to 3 carbon atoms or absolute methanol,
b) separating the organic solvent by concentrating the solvent up to a content of not more than 10% by weight, wherein water can be added in the last distillation steps,
c) diluting the remaining aqueous solution with water to a content of solids of 5 to 25% by weight, cooling to a temperature of below 25° C. and allowing it to stand until a precipitate forms,
d) a treatment of the remaining aqueous solution with ammonium sulfate and thereafter at least one extraction with methyl ethyl ketone or a mixture of methyl ethyl ketone and acetone,
e) concentrating the obtained extract and diluting with an ethanol-water mixture to a solution containing each 50% by weight water and ethanol and 10% by weight of solids,
f) treatment of the solution with a lead compound or an insoluble polyaminde,
g) filtration of the solution and passage through a strongly acidic cation exchanger, elution of the cation exchanger with aqueous ethanol or aqueous methanol,
h) treating the eluate with activated charcoal,
i) extraction of the filtered solution with an aliphatic or cycloaliphatic solvent having a boiling point of 60 to 100° C.,
j) concentrating the remaining aqueous-alcoholic solution, subsequently treating with ammonium sulfate and extraction with methyl ethyl ketone and ethanol,
k) concentrating the obtained organic phase to a content of solids of 50 to 70% by weight, and
l) drying the concentrate under vacuum to a dry extract having a water content of below 5%.

3. Method according to claim 2, wherein steps g) and h) are interchanged.

4. Method according to claim 2 wherein steps g) and h) are performed only after step i).

5. Medicament comprising a content of ginkgo biloba extract according to claim 1.

6. Use of the extract according to claim 1 for the preparation of a pharmaceutical formulation for the treatment of performance disturbances caused by cerebral insufficiency, peripheral occlusive disease, vertigo and tinnitus.

7. Method of treating a human to alleviate performance disturbances caused by cerebral insufficiency, peripheral occlusive disease, vertigo and tinnitus, wherein the method comprises administering to the human an effective amount of the extract according to claim 1.

8. Extract from ginkgo biloba leaves as recited in claim 1, wherein the alkyl phenol compounds are present in an amount below 1 ppm.

9. Method according to claim 3, wherein steps g) and h) are performed only after step i).

10. Method of treating a human to alleviate performance disturbances caused by cerebral insufficiency, peripheral occlusive disease, vertigo and tinnitus, wherein the method comprises administering to the human an effective amount of the medicament according to claim 5.

* * * * *